United States Patent [19]

Vidrine, Jr.

[11] Patent Number: 4,943,721

[45] Date of Patent: Jul. 24, 1990

[54] METHOD OF OBTAINING ACCURATE COMPOSITIONAL INFORMATION OF MULTI-LAYER COMPOSITIONS

[75] Inventor: Warren D. Vidrine, Jr., San Jose, Calif.

[73] Assignee: Measurex Corporation, Cupertino, Calif.

[21] Appl. No.: 370,420

[22] Filed: Jun. 22, 1989

[51] Int. Cl.$^5$ .................. G01N 23/02; G01N 21/35
[52] U.S. Cl. ................................ 250/308; 250/341; 250/339; 250/358.1; 250/359.1
[58] Field of Search ............. 250/308, 359.1, 358.1, 250/339, 341

[56] References Cited

U.S. PATENT DOCUMENTS

| | | | |
|---|---|---|---|
| 4,243,882 | 1/1981 | Yasujima et al. | 250/358.1 |
| 4,289,964 | 9/1981 | Baker | 250/308 |
| 4,574,194 | 3/1986 | Coats et al. | 250/308 |

Primary Examiner—Carolyn E. Fields
Attorney, Agent, or Firm—Burns, Doane, Swecker & Mathis

[57] ABSTRACT

The present invention relates to a method, or process, for deriving compositional information from a multi-layer composition which includes the steps of obtaining multi-layer fractional composition information using a non-contact gauge such as an FTIR gauge; obtaining additional multi-layer composition information using a beta gauge; and, correcting for beta ray absorption differences among the layers of the multi-layer composition by combining the multi-layer fractional composition information with the additional multi-layer composition information obtained using the beta gauge.

22 Claims, 1 Drawing Sheet

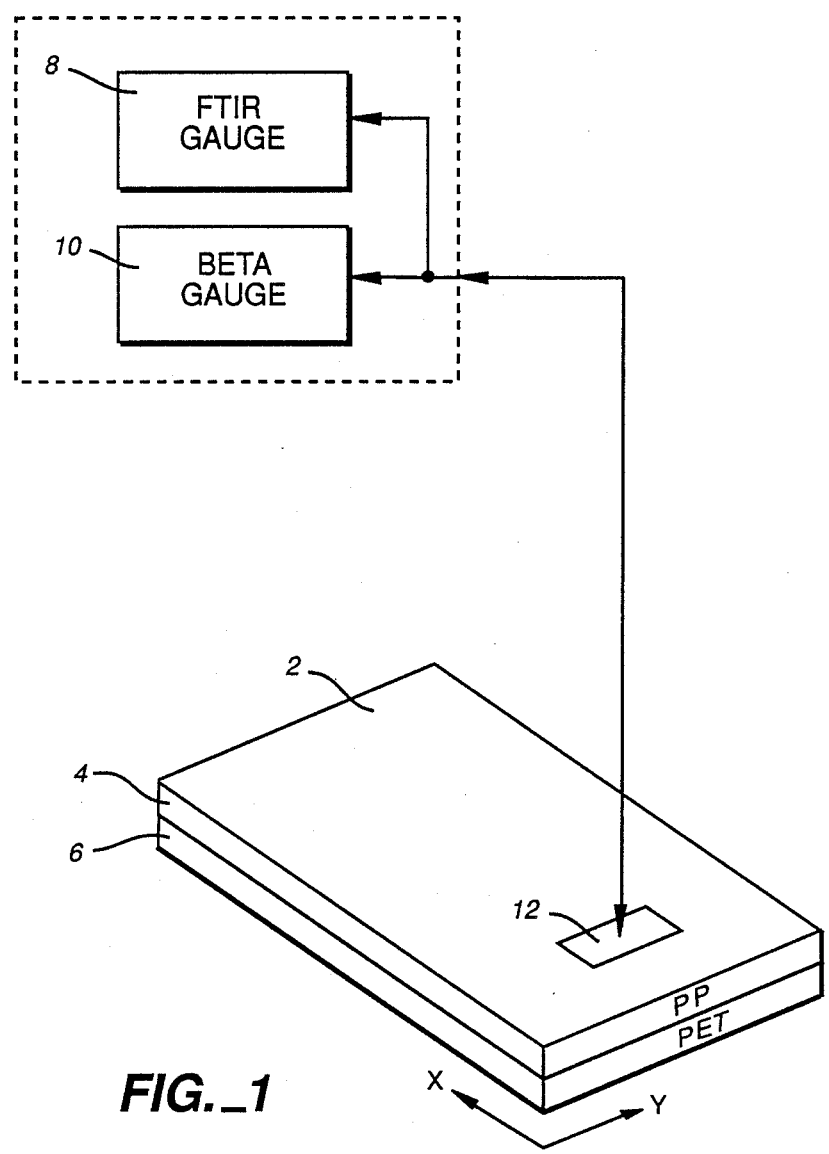
FIG._1

METHOD OF OBTAINING ACCURATE COMPOSITIONAL INFORMATION OF MULTI-LAYER COMPOSITIONS

BACKGROUND OF THE INVENTION

The present invention relates generally to a method of deriving compositional information. More specifically, the present invention relates a method of deriving accurate compositional information from a multi-layer composition.

Beta gauges are nuclear measuring devices which emit beta rays, and which have been used to measure characteristics of single-layer compositions, such as single-layer plastic films. For example, beta gauges have been used to measure the mass and/or thickness of these single-layer compositions.

Typically, a single-layer composition, such as a single-layer plastic film, has a known beta ray absorption coefficient (represented as a nominal composite KCM) and a known density. Using a beta gauge, the mass per unit area (usually represented as grams per square meter, or gsm) of the single-layer plastic film can be determined. That is, by multiplying the relatively accurate, raw output of the beta gauge by the known absorption coefficient of the single-layer plastic film, the mass per unit area can be calculated for each point on the film to be measured. Similarly, the thickness of the single-layer plastic film may be measured at each such point. The thickness of a point on the film corresponds to the mass per unit area of that point, as previously determined, divided by the known density of the plastic used to form the film.

Because the absorption coefficient and density for a given plastic are known with a relatively high accuracy, the beta gauge is relatively accurate in determining such characteristics as mass and thickness for a single-layer plastic film. For single-layer or single-component samples, the intrinsic accuracy of the beta gauge is approximately a quarter of a percent. That is, the output of the beta gauge can be used to calculate both the mass and the thickness of a single-layer plastic film to within a quarter of a percent.

However, the accuracy of the beta gauge deteriorates when a composition formed of multiple layers of different plastics is measured. For different plastics, the absorption coefficient for the beta rays varies. Similarly, the densities of different plastics are not the same. For example, the absorption of beta rays by different plastics can vary by as much as 4 to 5 percent. The densities of various plastics can vary by as much as 30 percent.

Thus, if a composition is formed from a plurality of layers of different materials, then the composite absorption coefficient for the entire multi-layer composition is unknown. If a composite absorption coefficient for the multi-layer material is merely estimated based on the range of potential values as mentioned above, then the total mass measurement of the multi-layer composition using a beta gauge could be off by as much as 4 to 5 percent. That is, because the mass of a composition is measured by multiplying the output of the beta gauge by the absorption coefficient and because the range of absorption coefficients for different plastics can vary as much as 4 to 5 percent, the accuracy of the beta gauge is limited to 4 to 5 percent in determining the mass of a multi-layer plastic. Typically, however, the beta gauge deteriorates from its quarter of a percent accuracy to approximately a 2 percent range of accuracy, since the particular plastics used to form a given multi-layer composition may have absorption coefficients which only vary in range by 2 percent.

Similarly, the accuracy of the beta gauge deteriorates when the gauge is used to measure the thickness of a multi-layer composition such as a multi-layer plastic film. As described above, the thickness of such a film can be determined by dividing the mass per unit area at a point on the film (as determined with the beta gauge and the absorption coefficient of the film) by the density of the plastic used to form the film. However, the accuracy of the beta gauge's mass determination for multi-layer compositions is relatively inaccurate, as was mentioned above. Furthermore, as with the absorption coefficient, the density of a multi-layer composition is not known with great accuracy.

That is, although the densities for the individual layers of a multi-layer plastic are known, the overall density for a given combination of plastic layers is not known. Rather, only the range of the densities for the various layers is known. As was mentioned above, the densities of the various layers in a multi-layer composition can vary by as much as 30 percent or more for different combinations of plastics.

Because the use of a beta gauge results in a mass per unit area measurement which is only known with approximately a 4 to 5 percent accuracy, and because the density of a multi-layer composition is only known with approximately a 30 percent accuracy, the compositional information such as the thickness of a multi-layer plastic which is derived from a beta gauge output is extremely limited in accuracy. Although the thickness derived from a beta gauge could be off by as much as 30 percent, a 5 to 10 percent error is typical. The accuracy of the information derived from a beta gauge deteriorates to a greater extent as the number of layers of different materials used to form the multi-layer composition is increased.

Such inaccuracies in the information derived from a beta gauge for a particular multi-layer composition are extremely serious. That is, a range of errors from 5 to 30 percent for multi-layer compositions is significantly greater than the subpercent accuracy which is typically associated with the use of a beta gauge for single-layer plastics.

The beta gauge's characteristics thus result in significantly less accurate readings when measuring compositions such as multi-layer plastic film constructions. This is especially true when mass and thickness measurements are required. The inaccuracy results from the fact that the relative composition of a multi-layer film varies. Therefore, the use of a single standard sample obtained from a multi-layer plastic sheet or film to derive mass and thickness measurements would not represent the composition of many or most of a sheet or film being produced. That is, the values for the beta gauge's primary calibration coefficients, (i.e., the absorption coefficient (KCM) and the density), would be accurate for the single standard sample but would not be accurate for most of the sheet or film which has been produced. The absorption coefficient and the composite density vary between such common low-density resins as polypropylene (PP) or polyethylene (PE), and such high-density, heteroatom-containing resins as nylon or polymethyl methacrylate (PMMA). Thus, relevant values for a composite absorption coefficient and a composite density of a multi-layer film can only be calculated if the composition of the film is known at each point on the film.

One area where improved accuracy in such compositional information as mass and thickness would be desirable is in the production of a multi-layer film or sheet as referred to above. Here, it is often desirable to maintain a tight tolerance on total film thickness both across the film as well as along the film. However, a thickness profile calculated from a beta gauge alone is extremely inaccurate for a multi-layer film. Attempts to modify the ratio of one layer to the next during the production of such a multi-layer film using, for example, the single standard sample referred to previously, merely result in false, or improper, thickness adjustments.

Accordingly, there is a need for a method of obtaining compositional information for multi-layer compositions, such as multi-layer plastics, which approaches the accuracy of the measurements derived for single-layer compositions.

SUMMARY OF THE INvENTION

The present invention therefore relates to a method, or process, for overcoming the deficiencies discussed above. More specifically, the present invention relates to a method, or process, for deriving compositional information from a multi-layer composition which includes the steps of:

obtaining multi-layer fractional composition information using a non-contact gauge, such as an FTIR gauge;

obtaining additional multi-layer composition information using a beta gauge; and, correcting for beta ray absorption differences among the layers of the multi-layer composition by combining the multi-layer fractional composition information with the additional multi-layer composition information obtained using the beta gauge.

In addition, the present invention relates to a process for measuring the composite mass of a multi-layer composition which includes the steps of:

obtaining a known absorption coefficient for each material forming a layer of the composition;

measuring the fractional composition of each layer forming the multi-layer composition with a first non-contact gauge;

determining a nominal composite absorption coefficient for the multi-layer composition using the absorption coefficient of each layer and the fractional composition of each layer;

measuring the multi-layer composition with a beta gauge to produce an output; and, determining the composite mass of the multi-layer composition using the nominal composite absorption coefficient and the beta gauge output.

In addition, the present invention relates to a process for measuring the composite thickness of a multi-layer composition which includes the steps of:

obtaining a known absorption coefficient and a known density for each material forming a layer of the composition;

measuring the fractional composition of each layer forming the multi-layer composition with a first non-contact gauge;

determining a nominal composite absorption coefficient for the multi-layer composition using the absorption coefficient of each layer and the fractional composition of each layer;

measuring the multi-layer composition with a beta gauge to produce an output;

determining a composite mass of the multi-layer composition using the nominal composite absorption coefficient and the beta gauge output;

determining a composite density of the multi-layer composition using the fractional composition of each layer and the known density of each layer; and, determining the composite thickness of the multi-layer composition using the composite mass and the composite density.

The present invention allows considerably better accuracy in obtaining compositional information for multi-layer compositions. In addition, the invention allows non-contact gauging of multi-layer compositions or constructions to be performed with enhanced accuracy.

The present invention is premised on the discovery that knowing the fractional composition of a multi-layer composition, even approximately, allows the values for a composite absorption coefficient and a composite density to be refined over the usual nominal or blind guesses. This permits the final beta gauge accuracy to be improved when the output values are expressed in, for example, mass or thickness units. Similarly, knowing the composition profile across the sheet, even approximately, allows absorption coefficient and density profiles to be developed. Such profiles supply individual absorption coefficient and density values for each individual beta thickness calculation. Inaccuracies associated with an assumption that the composite absorption coefficient and the composite density across the multi-layer sheet are constant can thus be avoided.

The method of the present invention thus enables a relatively accurate detection of such measurements as the mass (or weight) and thickness of a multi-layer plastic film. Such measurements are extremely beneficial during, for example, a process whereby a sheet or film formed of multiple layers of plastics is performed.

BRIEF DESCRIPTION OF THE DRAWINGS

Other objects and advantages will become apparent from the following detailed description of preferred embodiments of the invention as described in conjunction with the accompanying drawing wherein:

FIG. 1 shows a multi-layer film from which compositional information can be derived using the preferred method of the present invention.

DESCRIPTION OF THE PREFERRED EMBODIMENTS

As mentioned previously, the present invention relates to a process for deriving compositional information from a multi-layer composition. For purposes of the present invention, specific reference will be made to multi-layer compositions constructed of plastic layers. It will be appreciated, however, that the present invention could be utilized with other compositions or constructions with which a beta gauge is normally used to obtain compositional information such as mass or thickness.

In a preferred embodiment, the present invention relates to a process for measuring the mass of a multi-layer composition and a method for measuring the thickness of a multi-layer composition. The present invention enables not only the overall, or composite, mass and thickness of a multi-layer composition to be determined, but also allows the mass and thickness of an individual layer of the multi-layer composition to be determined with relatively high accuracy.

In general, compositional information of a multi-layer composition, such as a film or sheet constructed of multiple layers of different plastics, is determined in accordance with a preferred embodiment of the present invention by obtaining multi-layer fractional composition information using a non-contact gauge. For purposes of the present invention, fractional composition information refers to information indicative of the percentage of a multi-layer composition formed by each layer of the composition. A "non-contact" gauge refers to a gauge which does not itself physically touch the multi-layer composition to obtain the fractional composition information, as does, for example, a caliper-like gauge.

The output of an FTIR gauge can, for example, provide fractional composition information related to the mass per unit area of each layer in a multi-layer composition to within a 2 percent accuracy. The accuracy of the FTIR gauge does not vary significantly with an increased number of layers. For example, as the number of layers of different plastics used to form a multi-layer composition is increased, the accuracy of the FTIR gauge would likely retain an accuracy of at least 3 percent.

Knowing the fractional portion formed by each layer of a multi-layer composition to within 2 percent allows a composite absorption coefficient to be determined for the multi-layer composition with roughly a 2 percent accuracy. Similarly, a composite density for the multi-layer composition can be determined with roughly a 2 percent accuracy. The manner by which a composite absorption coefficient and a composite density are determined will be discussed more fully below.

The method of the present invention further includes the step of obtaining additional multi-layer composition information using a beta gauge in a manner as described previously. That is, the beta gauge is used to obtain a raw output value from which mass and thickness information for the multi-layer composition can be derived. However, because absorption coefficient differences and density differences among the layers of a multi-layer composition limit the accuracy of the beta gauge, the mass and thickness of the multi-layer composition are determined in the following manner.

In accordance with a preferred embodiment of the present invention, beta ray absorption differences of the multi-layer composition are corrected by combining the multi-layer fractional composition information obtained via the FTIR gauge with the additional multi-layer composition information obtained via the beta gauge as will be described below. Similarly, density differences of the multi-layer composition are corrected by combining the multi-layer fractional composition information obtained via the FTIR gauge with the additional multi-layer composition information obtained by the beta gauge.

For example, using the composite absorption coefficient for the multi-layer composition as determined with the 2 percent accuracy of an FTIR gauge, a more accurate conversion of the beta gauge output to a mass measurement can be obtained. Furthermore, the composite density as determined with the 2 percent accuracy of the FTIR gauge can be combined with the more accurate mass measurement as derived above to provide an improved thickness for the multi-layer composition.

A preferred embodiment of the present invention will now be described in greater detail. For purposes of the following discussion of a preferred embodiment, particular reference is made to a multi-layer composition consisting of two layers of plastics to provide a practical illustration of the features and the advantages which the present invention offers. That is, for the plastic film 2 shown in FIG. 1, a first layer is formed of polypropylene (PP) and a second layer is formed of Mylar (polyethylene terephtalate (PET)). The polypropylene layer is represented as the layer 4 in FIG. 1 and the Mylar is represented as the layer 6. It will be appreciated, however, that the present invention can be utilized with other types of multi-layer compositions or constructions in which it is desired to obtain compositional information via the use of a beta gauge.

For example, the accuracy of the present inventive method would not be seriously degraded when measuring a multi-layer composition formed of greater than 2 layers of different plastics. Such a multi-layer composition could, for example, include a 5 layer composition formed with a layer of polypropylene, a layer of PMMA, a layer of nylon, a layer of ethylvinyl alcohol (EVA) and a layer of (MAE). Other multi-layer constructions might include, for example, high-value constructions, such as those containing polypropylene and nylon; polyethylene, MAE and nylon; polypropylene, EVA and PMMA; or polypropylene and PMMA (just to name a few). Such constructions have similar disparities in absorption coefficient and density values among their multiple layers relative to the composition shown in FIG. 1.

In accordance with a preferred embodiment of the present invention, a process for measuring the mass and thickness of a multi-layer composition includes the step of obtaining a known absorption coefficient and a known density for each material forming a layer of the composition. As mentioned previously, the absorption coefficients and the densities of the plastics used to form a multi-layer composition generally constitute a priori knowledge, which is known relatively accurately. The known absorption coefficients and the known densities for each of the plastics or other materials included in the composition can, for example, be placed in a look-up table for later access during the process of the present invention. For purposes of the following discussion, the absorption coefficients for polypropylene and Mylar are represented as KCM(PP) and KCM(PET), respectively. The densities of polypropylene and Mylar are represented as D(PP) and D(PET), respectively.

In accordance with the method of the present invention, the fractional composition of each layer forming the multi-layer composition is measured with a non-contact gauge. For example, as was discussed previously, an FTIR gauge 8, as shown in FIG. 1, can be used to measure the fractional mass per unit area for each layer of the composition at a desired point on the composition. Such a measurement of the fractional portion represented by each layer is approximately 2 percent accurate as noted above.

For purposes of the present discussion, a raw value for the mass per unit area of each point on the polypropylene layer 4 measured by the FTIR gauge will be represented as the value VP. A raw value for the mass per unit area of each point on the Mylar layer 6 measured by the FTIR gauge will be represented as the value VT.

Using the values of VP and VT, the fractional portion of the sheet 2 represented by each of the polypropylene and Mylar layers can be determined. The fractional portion of the polypropylene at a currently measured point will be represented as FP. The fractional portion of the Mylar layer at the same measured point will be represented as FT. Using the mass per unit area measurements of the polypropylene and the Mylar as detected by the FTIR gauge (i.e., VP and VT, respectively), the fractional portions FP and FT of the polypropylene and Mylar layers can be determined using the following relationships:

$$FP = VP/(VP + VT)$$

$$FT = VT/(VP + VT)$$

The value (VP+VT) in the foregoing equations represents the total mass per unit area of the multi-layer composition as determined using the FTIR gauge.

A nominal composite absorption coefficient is determined for the multi-layer composition using the known absorption coefficient of each layer and the fractional composition of each layer. That is, the nominal composite absorption coefficient for the multi-layer composition is obtained by multiplying the absorption coefficient for each material forming a part of the multi-layer composition by the fractional portion of that material which is present at the point currently being measured, and summing the results. The composite absorption coefficient can thus be represented as KCM(FTIR), where:

$$KCM(FTIR) = (FP\ KCM(PP)) + (FT\ KCM(PET))$$

The multi-layer composition is also measured with a beta gauge to produce an output. The raw value output by the beta gauge is represented as VB. For single-layer compositions, this output VB is typically converted to a mass per unit area measurement by multiplying it with the absorption coefficient of the material being measured, as previously mentioned. A mass per unit area measurement (in gsm units) of the material being measured solely by a beta gauge can thus be represented as V(beta, gsm), where:

$$V(beta,\ gsm) = VB \cdot KCM$$

In accordance with the present invention, the composite mass of a multi-layer composition such as that shown in FIG. 1 is detected by using the nominal composite absorption coefficient and the output of the beta gauge. A composite mass (in gsm units) for a multi-layer composition as determined through the combined use of an FTIR gauge and a beta gauge can be represented as V(beta and FTIR, gsm), where:

$$V(beta\ and\ FTIR,\ gsm) = VB \cdot KCM(FTIR)$$

The nominal composite absorption coefficient as determined with an FTIR gauge is thus used in the foregoing equation to convert the raw value (VB) of the beta gauge into a mass per unit area value having roughly a subpercent accuracy. The accuracy of the beta gauge in measuring the composite mass of a multi-layer composition thus approaches the accuracy typically associated with beta gauge mass measurements for single-layer compositions.

To derive a composite thickness of a multi-layer composition in accordance with a preferred embodiment of the present invention, a composite density is determined using the fractional composition of each layer of the multi-layer composition (i.e., FP and FT) and the known density of each layer i.e., (D(PP) and D(PET)). A determination similar to that which was used for the calculation of a composite absorption coefficient in conjunction with the FTIR gauge is also used for the calculation of a composite density. That is, a composite density using the information supplied by the FTIR gauge is represented as D(FTIR), where:

$$D(FTIR) = 1/((FP/D(PP)) + (FT/DA(PET)))$$

Using the composite mass and the composite density, a composite thickness of the multi-layer composition can be determined using the following relationship:

$$Thickness = Mass/Density$$

The composite thickness of a multi-layer composition can thus be determined by dividing the composite mass as derived using the FTIR and the beta gauges by the composite density as derived using the FTIR gauge. Because the composite mass is determined to within a subpercent accuracy via the combined use of an FTIR gauge and a beta gauge, and because the composite density is determined to within a 2 percent accuracy using the FTIR gauge, a subpercent thickness measurement can thus be obtained. This thickness measurement is represented by the value V(FTIR and beta, thickness), where:

$$V(FTIR\ and\ beta,\ thickness) = V(FTIR\ and\ beta,\ gsm)/D(FTIR)$$

A thickness measurement could be obtained using only the FTIR gauge. That is, for the multi-layer composition shown in FIG. 1, a composite mass determined solely through the use of an FTIR gauge could be represented as V(FTIR, gsm), where:

$$V(FTIR,\ gsm) = VP + VT$$

In the foregoing equation, the value (VP+VT) thus represents the raw value of the FTIR gauge in mass per unit area for the polypropylene and Mylar layers of the FIG. 1 composition, respectively. Because the composite density D(FTIR) was also determined using the FTIR gauge as described above, a thickness could be calculated for the FIG. 1 composition using only the FTIR gauge, and could be represented as V(FTIR, thickness), where:

$$V(FTIR,\ thickness) = V(FTIR,\ gsm)/D(FTIR)$$

However, as noted previously, output values using the FTIR gauge can only be determined to roughly within a 2 percent accuracy. The composite absorption coefficient and density measurements are therefore obtained by the FTIR gauge with roughly the same 2 percent accuracy. It is only by combining the 2 percent accuracy of the FTIR gauge with the accurate output of a beta gauge in accordance with the preferred method of the present invention that measurements such as mass and thickness can be achieved for a multi-layer composition with an accuracy which exceeds an accuracy associated with the use of either such gauge independently.

A specific example of a measured point 12 on the FIG. 1 sheet will now be provided. The exemplary sheet 2 shown in FIG. 1 happens to have exactly 50 gsm of polypropylene (PP, KCM=1.04, density=0.903) and 50 gsm of Mylar (PET, KCM=1.00, density=1.370) at the currently measured location 12, giving a thickness of 91.87 microns at that point on the sheet. However, the relative layer weights vary approximately 20 percent root mean square (40/60 to 60/40), and for a 95 percent (2-sigma) confidence level the layer weights vary between a 30/70 ratio and a 70/30 ratio. This variation in relative weights exists across the sheet in a Y direction, and to a lesser extent along the length of the sheet in an X direction.

Using the preferred method as described above, an on-line mass and thickness measurement can be obtained with a sufficient accuracy and reliability to permit irregularities in mass and thickness of the layers to be corrected. Thus, the present inventive method permits relatively strict tolerances in mass and thickness of multi-layer films or sheets to be maintained so as to allow manufacturing process control of multi-layer plastic films or sheets.

For example, during the process of manufacturing a multi-layer film, extruders are provided to supply the various plastics which are to form each of the layers of a multi-layer composition. Controls are associated with each of these extruders so as to permit variations in thickness of the plastic derived therefrom to be regulated. Using variations in mass and thickness as detected in accordance with the preferred method of the present invention, the extruders can be adjusted in an online fashion. That is, the extruders can be controlled during the manufacture of a multi-layer composition to produce a composition having layers which are relatively uniform in mass and thickness.

The table below provides a comparison of measurements derived through the sole use of a beta gauge, the sole use of an FTIR gauge and the combined use of a beta gauge and an FTIR gauge for the multi-layer composition shown in FIG. 1.

| Gauge used for Calculations: | Beta alone | FTIR alone | Beta + FTIR Combined |
|---|---|---|---|
| (1) Real Value, total gsm | (100) (100) | (100) (100) | (100) |
| (2) Real values, PP & PET layers | (50, 50) | (50, 50) | (50, 50) |
| (3) Real value, micron thickness | (91.87) | (91.87) | (91.87) |
| (4) Raw 2-sigma deviation, % | (0.25%) | (2.0%) | (0.25% & 2.0%) |
| (5) Example raw value outliers | (97.79 to 98.29) | (98 to 102) | (97.79 to 98.28) |
| (6) Error in composition, % | (40%) | (2%) | (2%) |
| (7) Outliers, PP gsm | (30 to 70) | 49 to 51 | 49 to 51 |
| (8) Outliers, PET gsm | (30 to 70) | 49 to 51 | 49 to 51 |
| (9) True value for composite KCM | (1.020) | (1.020) | (1.020) |
| (10) Error in composite KCM | 0.008 | 0.0004 (N/A) | 0.0004 |
| (11) Error in composite KCM, % | 0.8% | 0.04% (N/A) | 0.04 |
| (12) Outliers in composite KCM | 1.012, 1.028 | 1.0196, 1.0204 | 1.0196, 1.0204 |
| (13) Total gsm 2-sigma deviation | 0.84% | 2% | 0.252% |
| (14) Outliers, final gsm | 98.96, 101.03 | 98.00, 102.00 | 99.71, 100.28 |
| (15) True composite Density | (1.0885) | (1.0885) | (1.0885) |
| (16) Error in composite Density | 0.09 | 0.0082 | 0.0082 |
| (17) Error in composite Density, % | 8.3% | 0.41% | 0.41% |
| (18) Outliers in Composite Density | 1.0059, 1.186 | 1.0841, 1.093 | 1.0841, 1.093 |
| (19) Total thickness 2-sigma dev. | 8.34% | 2.00% | 0.48% |
| (20) Outliers in Thickness, microns | 83.4, 100.4 | 90.0, 93.7 | 91.23, 92.50 |

As can be seen from the foregoing table, while the total mass deviation is 0.84 percent using the beta gauge and 2 percent using the FTIR gauge, a mass determination can be made with approximately a quarter of a percent accuracy when the beta gauge and the FTIR gauge are combined in accordance with the preferred embodiment of the invention (see line 13 of the table). For the thickness determination, an accuracy of 8.34 percent is obtained using the beta gauge, and an accuracy of 2 percent is obtained using the FTIR gauge. However, by combining the use of a beta gauge and an FTIR gauge in accordance with the present inventive method, an accuracy of greater than one half of a percent is obtained (see line 19 of the table) for a multi-layer composition as shown in FIG. 1. In the table, an Outlier analysis was used to derive the worst possible error for each of the measurements associated with the FIG. 1 multi-layer composition. The results of this Outlier analysis can be seen in lines 7, 8, 12, 14, 18 and 20 of the foregoing table.

Thus, it should be apparent from the foregoing table that beta measurements will be improved by the synergistic use of an FTIR gauge with a beta gauge whenever an expected range of component layer mass (weight) ratios is larger than the error in the FTIR measurement of those layers. A significant improvement in the accuracy of thickness measurements can also be expected with regard to multi-layer compositions which include layers containing barriers to beta rays transmitted from a beta gauge.

In accordance with the inventive method of the present invention, the composite absorption coefficient and density for a multi-layer composition can be calculated by grouping materials forming layers of a multi-layer composition even when not all of the materials which are used to compose the film can be measured by the FTIR. That is, when the characteristics associated with one layer of a multi-layer composition are so similar to another layer that the layers cannot be distinguished by an FTIR gauge, these layers will generally have similar absorption coefficient and density values and can be grouped together, or considered to represent a single layer by the FTIR gauge. Such an approximation will not significantly affect the mass and thickness measurements which are obtained via the combined use of the FTIR gauge and the beta gauge as described previously.

In addition, by determining the mass and/or thickness of a plurality of points of a multi-layer composition in accordance with the inventive method, composite absorption coefficient and composite density profiles for the multi-layer composition can be developed. Such profiles can, for example, be interpolated to permit mass and thickness determinations to be made with a beta gauge at any point on the multi-layer composition.

Thus, the present invention enables the composite mass and thickness of a multi-layer composition to be determined with an accuracy which approaches that associated with measurements for single-layer compositions. In addition, the present invention enables the mass and thickness of particular layers of a multi-layer composition to be obtained with similar accuracy. That is, having accurately determined the composite mass and composite thickness of a multi-layer composition using the beta gauge and the FTIR gauge as described above, the mass or thickness of a single layer can be determined by multiplying the composite mass or thickness by the fractional portions determined using the FTIR gauge (i.e., FP and FT in the exemplary discussion provided above).

It will be appreciated by those of ordinary skill in the art that the present invention can be embodied in other specific forms without departing from the spirit or essential characteristics thereof. The presently disclosed embodiments are therefore considered in all respects to be illustrative and not restrictive. The scope of the invention is indicated by the appended claims rather than the foregoing description, and all changes that come within the meaning and range of equivalents thereof are intended to be embraced therein.

What is claimed is:

1. Process for measuring the composite thickness of a multi-layer composition which comprises the steps of:
   obtaining a known absorption coefficient and a known density for each material forming a layer of the composition;
   measuring the fractional composition of each layer forming the multi-layer composition with a first non-contact gauge;
   determining a nominal composite absorption coefficient for the multi-layer composition using the absorption coefficient of each layer and the fractional composition of each layer;
   measuring the multi-layer composition with a beta gauge to produce an output;
   determining a composite mass of the multi-layer composition using the nominal composite absorption coefficient and the beta gauge output;
   determining a composite density of the multi-layer composition using the fractional composition of each layer and the known density of each layer; and,
   determining the composite thickness of the multi-layer composition using the composite mass and the composite density.

2. The process for measuring of claim 1, wherein the step of measuring the fractional composition of each layer of the multi-layer composition is performed by using an FTIR gauge.

3. The process for measuring of claim 1, wherein the multi-layer composition is a multi-layer film composed of plastics having different absorption coefficients and densities.

4. The process for measuring of claim 1, wherein said step of obtaining includes retrieving absorption coefficient data and density data from a look-up table.

5. The process for measuring of claim 1, wherein said step of measuring the fractional composition further includes the step of:
   determining the mass of each layer at a point on the multi-layer composition.

6. The process for measuring of claim 1, wherein the step of determining a nominal composite absorption coefficient includes the steps of:
   multiplying the known absorption coefficient of each layer by the fractional composition of each layer, respectively; and,
   summing the results of said multiplying step.

7. The process for measuring of claim 1, wherein the step of determining a composite density includes the steps of:
   multiplying the known density of each layer by the fractional composition of each layer, respectively; and,
   summing the results of said multiplying step.

8. The process for measuring of claim 1, further including the steps of:
   measuring the composite thickness of the multi-layer composition at a plurality of points on the composition; and,
   developing composite absorption coefficient and composite density profiles for the multi-layer composition using the composite thickness measurements.

9. The process for measuring of claim 1, further including the step of:
   determining the mass of a single layer of the multi-layer composition using the composite mass and the fractional composition of the single layer.

10. The process for measuring of claim 1, further including the step of:
    determining the thickness of a single layer of the multi-layer composition using the composite thickness and the fractional composition of the single layer.

11. A process for measuring the composite mass of a multi-layer composition comprising the steps of:
    obtaining a known absorption coefficient for each material forming a layer of the composition;
    measuring the fractional composition of each layer forming the multi-layer composition with a first non-contact gauge;
    determining a nominal composite absorption coefficient for the multi-layer composition using the absorption coefficient of each layer and the fractional composition of each layer;
    measuring the multi-layer composition with a beta gauge to produce an output; and,
    determining the composite mass of the multi-layer composition using the nominal composite absorption coefficient and the beta gauge output.

12. The process for measuring of claim 11, wherein the step of measuring the fractional composition of each layer of the multi-layer composition is performed by using an FTIR gauge.

13. The process for measuring of claim 11, wherein said step of obtaining includes retrieving absorption coefficient data from a look-up table.

14. The process for measuring of claim 11, wherein said step of measuring the fractional composition further includes the step of:
    determining the mass of each layer at a point on the multi-layer composition.

15. The process for measuring of claim 11, wherein the step of determining a nominal composite absorption coefficient includes the steps of:

multiplying the known absorption coefficient of each layer by the fractional composition of each layer, respectively; and, summing the results of said multiplying step.

16. Process for deriving compositional information from a multi-layer composition comprising the steps of:

obtaining multi-layer fractional composition information using a non-contact gauge;

obtaining additional multi-layer composition information using a beta gauge; and, correcting for beta ray absorption differences among the layers of the multi-layer composition by combining the multi-layer fractional composition information with the additional multi-layer composition information obtained using the beta gauge.

17. The process of claim 16, wherein the step of obtaining multi-layer fractional composition information is performed using an FTIR gauge.

18. The process for measuring of claim 16, wherein the multi-layer composition is a multi-layer film composed of plastics having different absorption coefficients and densities.

19. Process for producing a multi-layer composition formed from different plastics comprising the steps of:

deriving compositional information from the multi-layer composition during the production of the multi-layer composition; and, controlling the formation of each layer of the multi-layer composition on the basis of said compositional information, said step of deriving compositional information further including:

obtaining multi-layer fractional composition information using a non-contact gauge;

obtaining additional multi-layer composition information using a beta gauge; and, correcting for beta ray absorption differences among the layers of the multi-layer composition by combining the multi-layer fractional composition information with the additional multi-layer composition information obtained using the beta gauge.

20. The process of claim 19, wherein the step of obtaining multi-layer fractional composition information is performed using an FTIR gauge.

21. A multi-layer composition having layers formed from different plastics by a process which includes the steps of:

deriving compositional information from the multi-layer composition during the production of the multi-layer composition; and, controlling the formation of each layer of the multi-layer composition on the basis of said compositional information, said step of deriving compositional information further including:

obtaining multi-layer fractional composition information using a non-contact gauge;

obtaining additional multi-layer composition information using a beta gauge; and, correcting for beta ray absorption differences among the layers of the multi-layer composition by combining the multi-layer fractional composition information with the additional multi-layer composition information obtained using the beta gauge.

22. The process of claim 21, wherein the step of obtaining multi-layer fractional composition information is performed using an FTIR gauge.

* * * * *